United States Patent [19]

Pálosi et al.

[11] Patent Number: 4,465,855
[45] Date of Patent: Aug. 14, 1984

[54] PROCESS FOR THE PREPARATION OF ARYLACETIC ACID DERIVATIVES

[75] Inventors: Endre Pálosi; Dezsö Korbonits; Pál Kiss; Csaba Gönczy; Gergely Heja; Judit Cser née Kun, all of Budapest; Rudolf Szebeni, Göd; Maria Szomor née Wundele; Ida Szvoboda née Kanzel, both of Budapest, all of Hungary

[73] Assignee: Chinoin Gyogyszer es Vegyeszeti Termekek Gyara Rt, Budapest, Hungary

[21] Appl. No.: 368,721

[22] Filed: Apr. 15, 1982

Related U.S. Application Data

[62] Division of Ser. No. 246,414, Mar. 23, 1981, Pat. No. 4,385,004, which is a division of Ser. No. 041,106, May 21, 1979, Pat. No. 4,317,920.

[30] Foreign Application Priority Data

May 23, 1978 [HU] Hungary .............................. CI-1829

[51] Int. Cl.$^3$ ........................................... C07C 53/134
[52] U.S. Cl. .................................... 562/496; 562/490; 562/408; 562/426; 562/460; 562/465; 562/466; 562/469
[58] Field of Search ............... 562/408, 490, 496, 426, 562/460, 465, 466, 469

[56] References Cited

U.S. PATENT DOCUMENTS

2,899,465  8/1959  Girard et al. ...................... 562/408
3,870,753  3/1975  Tull et al. ............................. 562/496

FOREIGN PATENT DOCUMENTS

7093923  6/1982  Japan ..................................... 562/496
7704442  10/1977  Netherlands ......................... 562/496

Primary Examiner—Paul J. Killos
Attorney, Agent, or Firm—Karl F. Ross; Herbert Dubno

[57] ABSTRACT

Arylacetic acid derivatives of the formula

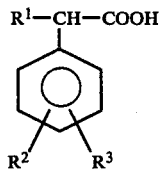

with $R^1$, $R^2$ and $R^3$ specifically defined and which are useful as antirheumatic and antiinflammatory pharmaceuticals are prepared by catalytic hydrogenation of new compounds of the formula

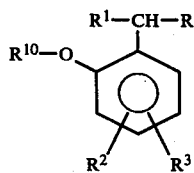

in which R and $R^{10}$ are also specifically defined. The method of making the latter compound is also set forth.

7 Claims, No Drawings

PROCESS FOR THE PREPARATION OF ARYLACETIC ACID DERIVATIVES

CROSS REFERENCE TO RELATED APPLICATIONS

This application is a division of Ser. No. 246,414 filed Mar. 23, 1981, now U.S. Pat. No. 4,385,004 which was a divisional of Ser. No. 041,106 filed May 21, 1979, now U.S. Pat. No. 4,317,920.

The present invention relates to a new process for the preparation of arylacetic acid derivatives of the formula I

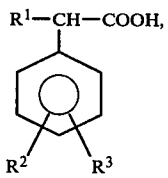

wherein
$R^1$ is hydrogen, methyl or ethyl;
$R^2$ is hydrogen, fluorine or an alkyl having 1 to 4 carbon atoms;
$R^3$ is hydrogen, phenyl, alkoxy having 1 to 6 carbon atoms, phenoxy or unsubstituted or substituted benzoyl or thenoyl; or
$R^2$ and $R^3$ together with the phenyl group they are attached to represent a naphthyl group which can be substituted with one or more alkyl and/or alkoxy groups having 1 to 4 carbon atoms.

Compounds of the formula I, wherein $R^1$, $R^2$ and $R^3$ are prepared according to the invention starting from compounds of the formula VIII

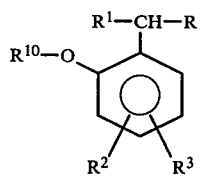

wherein
R is vinyl or carboxyl;
$R^{10}$ is phenylaminocarbonyl, 1-phenyl-5-tetrazolyl, 2-benzoxyazolyl, an —SO$_2$OMe group, wherein Me is a metal atom, preferably sodium or potassium, or an —SO$_2$R$^6$ group, wherein
$R^6$ is alkyl having 1 to 4 carbon atoms, 4-methylphenyl, amino, acylamino, alkoxycarbonylamino having 1 to 4 carbon atoms in the alkyl moiety or $R^{10}$ is an
$R^7$—N=C—NH—$R^7$ group, wherein
$R^7$ is alkyl having 1 to 4 carbon atoms, cycloalkyl having 5 or 6 carbon atoms or tolyl
and $R^1$, $R^2$ and $R^3$ have the meanings defined above.

Compounds of the formula VIII are new, and are also within the scope of this invention.

According to the invention compounds of the general formula I, wherein $R^1$, $R^2$ and $R^3$ have the meanings defined above, may be prepared by subjecting new arylacetic acid derivatives of the formula VIII, wherein $R^1$, $R^2$, $R^3$ and $R^{10}$ have the meanings defined above and R is carboxyl, to catalytic hydrogenation.

It is well known that many of the substituted arylacetic acid derivatives of the formula I possess valuable antirheumatic and antiinflammatory properties and have small side-effects. These compounds are widely used in human therapy. They are for example described in the U.S. Pat. No. 3,600,437; German Pat. No. 1,941,625; Belgian Pat. Nos. 621,225 and 787,417; British Pat. Nos. 971,700 and 1,132,318; French Pat. Nos. 1,545,270 and 1,549,729 as well as in the Hungarian Patent Application RO-687.

In the majority of the methods known for the preparation of the compounds of the formula I compounds of the formula XI

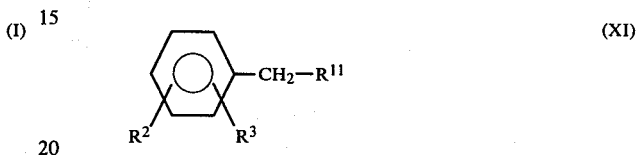

wherein $R^{11}$ is carboxyl, carbalkoand $R^2$ and $R^3$ are as defined, are reacted with alkylating agents of the formula XII $$R^1-X \qquad (XII)$$

wherein
$R^1$ has the same meaning as defined above and
X is halogen or a CH$_3$C$_6$H$_4$N=N—NH—group,
and, if desired, a compound obtained, in which $R^{11}$ is other than carboxyl, is converted into a corresponding compound of the formula I in a manner known per se. The reaction is illustrated on the following Chart A

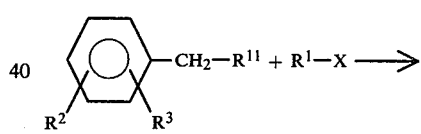

and is described in the German Pat. Nos. 1,668,648 and 1,941,625; U.S. Pat. Nos. 3,600,437 and 3,755,427, Belgian Pat. No. 752,627 and Holland Patent Application No. 74,06897.

A common feature of these processes is that their critical step is the formation of a C—C bond between the alkylating agent and the carbon atom adjacent to the carboxyl group. The reaction can either be performed with very moderate yields or yields the desired product through more intermediates, which are difficult to purify involving complicated technology.

According to other methods an α-substituted alkanecarboxylic acid group is introduced into a suitably substituted aryl ring by electrophilic substitution, and the product obtained is converted into a corresponding free acid. The reaction is illustrated on Chart B below:

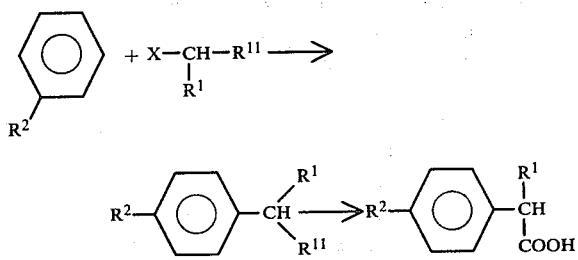

wherein $R^1$, $R^2$, $R^{11}$ and X have the above-defined meanings. Similar reactions are described in the British Pat. No. 971,700 and in the Belgian Pat. Nos. 621,225 and 748,534.

These processes can only restrictedly be used, partly due to a potential deactivating effect of certain substituents, e.g. keto group and partly because of their unsatisfactory selectivity.

Another group of known processes relates to the formation of a branch in the α-position of the alkanecarboxylic acid group by isomerization, as shown on Chart C:

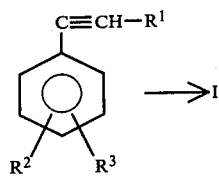

According to U.S. Pat. No. 3,803,245 thallic nitrate is used for this purpose. This method, however, because of the toxicity of thallium can be industrially used only very carefully, under special precautions.

It has now surprisingly been found that compounds of the formula I, wherein $R^1$, $R^2$ and $R^3$ are as defined above, can be prepared very easily by hydrogenating compounds of the formula VIII, in which R represents a carboxyl group, and $R^1$, $R^2$, $R^3$ and $R^{10}$ have the above-identified meanings.

In the compounds prepared and used according to the invention the terms "alkyl and alkoxy groups" refer to straight or branched chain hydrocarbon groups, such as methyl, ethyl, isopropyl, n-butyl, tertiary butyl and methoxy, ethoxy and isopropoxy.

In the definition of X the term "halogen" preferably represents chlorine, bromine or iodine.

In the definition of $R^6$ the term "acylamino" preferably indicates an optionally substituted benzoyl or an alkanoyl amino group having 1 to 5 carbon atoms, e.g. formyl, acetyl, and propionyl amino.

In the definition of $R^3$ and $R^6$ the substituents may be selected from the following groups: amino, nitro, $C_{1-4}$-alkylamino, $C_{1-4}$-alkyl-$C_{1-4}$-alkoxy, and halogen.

In the definition of Y the "halogen" is preferably to a chlorine or bromine group.

According to a preferred embodiment of the invention arylacetic acid derivatives of the general formula I are prepared by carrying out catalytic hydrogenation in water or in an organic solvent, preferably at a temperature between 20° to 90° C., under a pressure of 1 to 3 atm.

As organic solvents preferably alcohols, more particularly methanol or ethanol; benzene, dioxane; ethylacetate; dimethyl formamide or organic acids, more particularly acetic acid can be used. Reaction is preferably accomplished in the presence of an inorganic base, e.g. an alkali metal hydroxide, preferably sodium or potassium hydroxide; alkali metal alcoholate, preferably sodium methylate or sodium ethylate; or in the presence of an organic base, e.g. triethyl amine.

The compounds of the formula VIII are new as noted above. The present invention concerns also these compounds as well as a process for the preparation of same.

According to the invention compounds of the formula VIII, wherein R, $R^{10}$, $R^1$, $R^2$ and $R^3$ are as defined hereinbefore, are prepared by reacting hydroxyl derivatives of the formula V

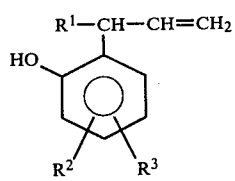

wherein $R^1$, $R^2$ and $R^3$ are as defined above,
(a) with compounds of the formula VI $$R^5-Y \qquad VI$$

wherein
$R^5$ is 1-phenyl-5-tetrazolyl, 2-benzoxazolyl or an —$SO_2R^6$ group, in which
$R^6$ has been defined above, and
Y represents halogen; or
(b) with phenylisocyanate; or
(c) with compounds of the formula IX $$R^7-N=C=N-R^7 \qquad IX$$

wherein $R^7$ has been defined above; or
(d) with compounds of the formula X

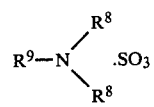

wherein
$R^8$ is alkyl having from 1 to 4 carbon atoms, and
$R^9$ is alkyl having from 1 to 4 carbon atoms or phenyl; or
(e) with a pyridine-sulphur trioxide complex, and, if desired oxidizing a compound of the general formula VIII obtained, in which R is a vinyl group into another compound of the formula VIII, in which R represents a carboxyl group.

A narrower group of the compounds of the formula VIII, more particularly compounds of the formula XIII

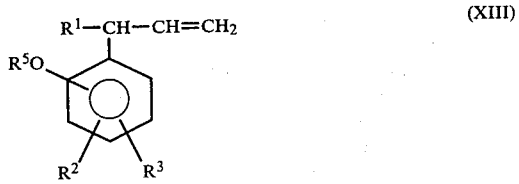

wherein $R^1$, $R^2$ and $R^3$ and $R^5$ are as defined hereinbefore, are prepared according to process variant (a) of the invention by reacting hydroxyaryl derivatives of the formula V, wherein $R^1$, $R^2$ and $R^3$ are as defined above, with methane sulphonylchloride, p-toluene sulphonylchloride, sulphaminic acid chloride, N-benzoyl-sulphaminic acid chloride or N-methoxy-sulphaminic acid chloride, in water and/or in organic solvents. This reaction is preferably carried out at a temperature of 0° C. to 40° C.

As an organic solvent pyridine, acetone, methylene chloride or benzene is preferably used and the reaction is preferably carried out in the presence of an inorganic base, e.g. alkali or alkali earth metal hydroxide or carbonate; or of an organic base, e.g. triethylamine.

According to a preferred embodiment of process variant (b) those compounds of the formula VIII, which can be encompassed by the formula XIV

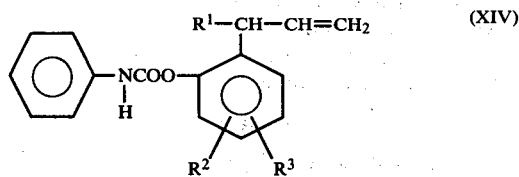

wherein $R^1$, $R^2$ and $R^3$ are as defined above, can be prepared by reacting a hydroxyaryl derivative of the formula V, in which $R^1$, $R^2$ and $R^3$ have the meanings defined above, with phenyl isocyanate, optionally in the presence of an organic solvent, preferably petroleum ether. The reaction is preferably carried out at a temperature of 20° C. to 100° C., in the presence of an alkaline catalyst, preferably pyridine.

According to process variant (c) those compounds of the formula VIII, which can be encompassed by the formula XV

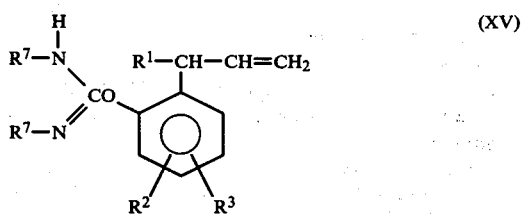

wherein $R^1$, $R^2$, $R^3$ and $R^7$ are as hereinbefore defined, are prepared by reacting a hydroxyaryl derivative of the formula V, wherein $R^1$, $R^2$ and $R^3$ have the meanings as defined above, with an excess amount of dicyclohexyl carbodiimide or di-p-tolyl-carbodiimide, in the absence of solvent, preferably at a temperature of 20° C. to 100° C.

According to process variant (d) those compounds of the formula VIII, which are encompassed by the formula V

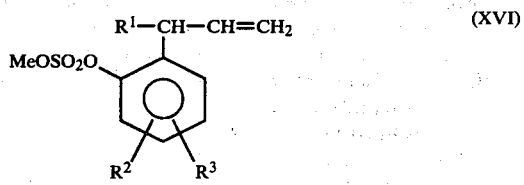

in which $R^1$, $R^2$, $R^3$ and Me are as hereinbefore defined, are prepared by reacting a hydroxyaryl derivative of the formula V, wherein $R^1$, $R^2$ and $R^3$ are as defined, with a sulphur trioxide complex of N,N-dimethylaniline, N,N-diethyl-aniline or trimethyl-aniline in an organic solvent, preferably in carbon disulphide or benzene, at a temperature of $-10°$ C. to $+40°$ C., and subsequently treating the reaction mixture with an aqueous solution of an inorganic base. The reaction is preferably carried out in the presence of an excess amount of a base (for example aqueous sodium or potassium hydroxide solution).

According to process variant (e) those compounds of the formula VIII, which are encompassed by the formula XVI, are prepared by reacting a hydroxyaryl derivative of the formula V, with pyridine-sulphur trioxide complex, in an organic solvent, preferably in carbon disulphide or benzene, at a temperature between $-10°$ C. and $+40°$ C., and treating the reaction mixture obtained with an aqueous solution of an inorganic base. The reaction is performed in the presence of an excess amount of aqueous sodium or potassium hydroxide solution.

The compounds of the formula VIII, in which R represents a vinyl group can be converted into corresponding compounds of the formula VIII, in which R is carboxyl by oxidation. The oxidation can, for example, be carried out with potassium permanganate, in the presence of an organic solvent, preferably at a temperature of 0° C. to 40° C. As an oxidizing agent an alkali metal periodate, preferably sodium or potassium periodate can also be successfully used. Suitable solvents are water and/or organic solvents, preferably tert.-amylalcohol, benzene, pentane, methylene chloride, acetone. According to an especially preferred embodiment of the process the process is carried out in the presence of a phase-transforming catalyst and acetic acid. As a catalyst preferably tetrabutyl ammoniumchloride, tetrabutyl-ammoniumbromide, triethyl-benzyl-ammoniumchloride, tricaprilyl-methylammoniumchloride, trioctyl-methyl-ammoniumchloride or benzylhexadecyl-dimethyl-ammoniumchloride or crown ether, preferably 18-crown-6 or dicyclohexyl-18-crown-6 can be used.

Of the compounds of the formula V which are used as starting compounds in the preparation of new compounds of the formula VIII, the following are new:
3-isobutyl-6-allyl-phenol,
3-isobutyl-6-(1-methyl-allyl)-phenol,
4-phenoxy-2-(1-methyl-allyl)-phenol,
4-phenoxy-2-allyl-phenol,
2-allyl-6-methoxy-naphthol,
2-(1-methyl-allyl)-naphthol, and
4-benzoyl-2-(1-methyl-allyl)-phenol.

The compounds of the formula V can be prepared in a manner known per se, by reacting compounds of the formula II

wherein $R^2$ and $R^3$ are as defined above, with compounds of the formula III

  (III)

and subjecting the obtained compounds of the formula IV

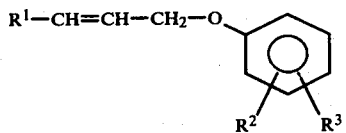  (IV)

to thermal isomerization.

The following compounds of the formula IV are new:
2-fluoro-5-allyloxy-diphenyl,
2-fluoro-5-crotyloxy-diphenyl,
(3-isobutylphenyl)-allyl-ether,
(3-isobutyl-phenyl)-crotyl-ether,
4-allyloxy-diphenylether,
4-crotyloxy-diphenylether,
4-crotyloxy-benzophenone,
1-allyloxy-6-methoxy-naphthalene, and
1-crotyloxy-6-methoxy-naphthalene.

The aryloxy derivatives of the formula IV are preferably prepared in water and/or in an organic solvent, preferably acetone, dimethyl formamide, ether, in the presence of a base, preferably potassium carbonate or sodium carbonate, at a temperature of 20° C. to 100° C.

The thermal isomerization of the compounds of the formula IV is preferably effected at 150° C. to 260° C., in the absence of solvent or in an organic solvent, preferably N,N-dimethylaniline, N,N-diethylaniline, dimethyl formamide or diphenyl ether.

According to the process provided by this invention compounds of the formula I can be prepared starting from compounds of the formula II in an entirely new manner, through new intermediates as illustrated on Chart D.

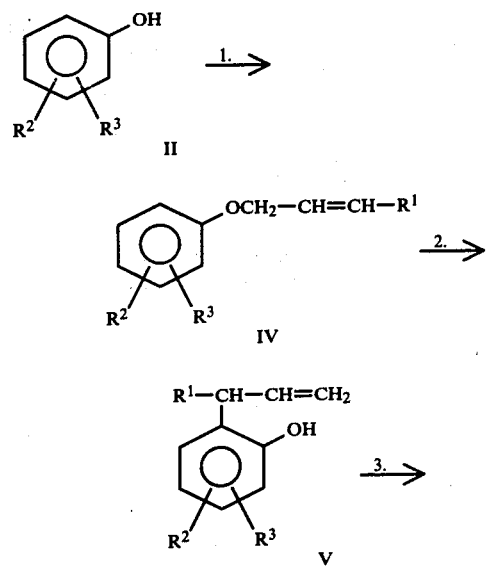

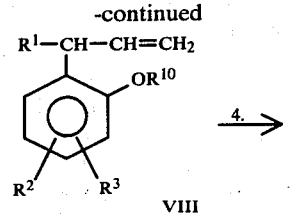

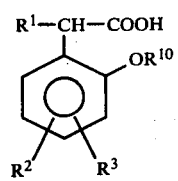

The process according to the invention is considerably easier to carry out also on an industrial scale than the processes known in the art.

Further details of the invention are illustrated by the following illustrative and non-limiting Examples.

EXAMPLE 1

To a solution of 19.8 g. of 4-hydroxy-benzophenone in 100 ml. of dry acetone 18.3 g. of crotyl bromide and 14 g. of anhydrous potassium carbonate are added. The reaction mixture is boiled for 4 hours with stirring and acetone is distilled off. The residue is treated with water and the separated oil is taken up in ether. The ethereal solution is washed with a dilute aqueous sodium hydroxide solution and subsequently with water, and is then dried over sodium sulphate. Upon distilling off of the ether 4-crotyloxy-benzophenone is obtained as a pale yellow oil, which crystallizes in one to two days to afford a product melting at 36° C.

EXAMPLE 2

A solution of 5 g. of 4-crotyloxy-benzophenene in 15 ml of diphenyl ether is boiled for one hour. It is allowed to cool and is diluted with petroleum ether. The solution obtained is extracted with a 5N sodium hydroxide solution. The alkaline phase is acidified with a dilute aqueous hydrochloride acid solution, the precipitated crystals are filtered off with suction and recrystallized from cyclohexane to give 4-benzoyl-2-(1-methyl)-allyl-phenol, melting at 111° C. to 113° C.

EXAMPLE 3

To a solution of 104 ml. of o-cresol in 200 ml. of acetone a solution of 40.8 g. of sodium hydroxide in 160 ml. of water is added. To the reaction mixture 104 ml. of crotyl bromide are added dropwise, with stirring under cooling with ice-water. Stirring is continued for a further 2 hours, whereupon the mixture is brought to the boil and boiled for an additional hour. After cooling the organic phase is separated, the aqueous phase is shaken with two 50-ml. portions of petroleum ether. The combined organic phases are shaken with eight 100-ml. portions of a 30% aqueous sodium hydroxide solution and washed to neutral with water. Upon the distilling off of petroleum ether o-cresol-crotyl ether is obtained as a yellow, oily residue.

o-cresol-crotyl ether obtained is refluxed until the boiling point arises to 210° C. (about 4 hours). After cooling 160 ml. of a 20% aqueous potassium hydroxide solution are added and the reaction mixture is shaken with three 50-ml. portions of petroleum ether. The aqueous solution is acidified with a concentrated hydrochloric acid solution. The separated oil is taken up in ether, the ethereal solution is washed to neutral with water and dried over sodium sulphate. Ether is distilled off and the remaining oil is subjected to distillation in vacuo to yield 2-methyl-6-(1-methyl)-allyl-phenol. $n_D^{25} = 1.5315$.

EXAMPLE 4

8.62 g. of 4-phenoxy-phenyl-crotyl ether (prepared according to DOS No. 2,304,962) in 30 ml. of diphenyl ether are refluxed for one hour at 260° C. The reaction mixture is cooled to room temperature, diluted with 30 ml. of petroleum ether and shaken with two 25-ml. portions of Claisen-alkali. The alkaline phase is acidified with a concentrated aqueous hydrochloric acid solution and shaken with three 30-ml. portions of ether. The combined ethereal phases are dried over sodium sulphate and evaporated to give 2-(1-methyl-allyl)-4-phenoxy-phenol.

EXAMPLE 5

To a solution of 48.7 g. of 2-allyl-phenol in 176 ml. of dry pyridine 34 ml. (51,3 g.) of mesyl chloride are added dropwise, with stirring, under cooling. The reaction mixture is allowed to stand for 2 hours and is then poured on a mixture of concentrated hydrochloric acid and ice. The precipitated oil is taken up in ether, the ethereal solution is washed with a 2N sodium hydroxide solution and subsequently with water, and is dried over sodium sulphate. Ether is distilled off to give 69.4 g. of 2-allyl-phenol mesylester. $n_D^{25} = 1.5191$.

EXAMPLE 6

To a cooled solution of 14.7 g. of 2-(1-methyl)-allyl-phenol in 50 ml. of dry pyridine 14.5 g. of mesyl chloride are added dropwise, with stirring. The reaction mixture is allowed to stand overnight, whereupon it is poured onto a mixture of concentrated hydrochloric acid and ice. The separated oil is taken up in ether. The ethereal solution is washed with a 2N sodium hydroxide solution and subsequently with water, and is then dried over sodium sulphate. Ether is distilled off to give 20 g. of 2-(1-methyl)-allyl-phenol mesylester. $n_D^{25} = 1.5197$.

EXAMPLE 7

Following the procedure described in Example 6 but replacing 2-(1-methyl)-allyl-phenol by 18.4 g. of 2-allyl-1-naphthol 20.5 g. of 2-allyl-1-naphthol mesylester are obtained as a slowly solidifying oil. The oily product crystallizes in 1 to 2 days and the melting point of the crystals obtained amounts to 45° C.

EXAMPLE 8

To a cooled solution of 33.8 g. of 2-allyl-phenol in 125 ml. of dry pyridine 47.5 g. of p-toluene-sulphonic acid chloride are added in small portions, with stirring. The mixture is stirred for three hours whereupon it is poured onto the mixture of concentrated hydrochloric acid and ice. Then the procedure described in Example 6 is followed. 2-allyl-phenol tosylester is obtained. $n_D^{25} = 1.5543$.

EXAMPLE 9

A mixture of 13.5 g. of 2-allyl-phenol, 13.1 g. of phenylisocyanate and 0.5 g. of pyridine is kept at 100° C. for five minutes. Petroleum ether is added whereupon the precipitated crystals are filtered off with suction and washed with petroleum ether to give 2-allyl-phenol-phenylurethane, melting at 108° C. to 109° C.

EXAMPLE 10

Following the procedure described in Example 9 but starting from 18.4 g. of 2-allyl-1-naphthol, 13.1 g. of phenyl-isocyanate and 0.5 ml. of pyridine and recrystallizing the product obtained from carbon tetrachloride 2-allyl-1-naphthol-phenyl-urethane is prepared, melting at 141° C. to 142° C.

EXAMPLE 11

Following the procedure described in Example 9 but starting from 3.4 g. of 2-(1-methyl)-allyl-phenol, 3.3 g. of phenyl-isocyanate and 0.1 ml. of pyridine 2-(1-methyl)-allyl-phenol-phenyl-urethane is obtained, melting at 92° C. to 94° C.

EXAMPLE 12

Following the procedure described in Example 9 but starting from 8.4 g. of 2-(1-methyl)-allyl-1-naphthol, 8.7 g. of phenyl-isocyanate and 0.2 ml. of pyridine 2-(1methyl)-allyl-1-naphthol-phenyl-urethane is obtained, melting at 138° C. to 142° C.

EXAMPLE 13

To a solution of 22 g. of 2-methyl-6-allyl-phenol [J. Org. Chem. 30, 1032 (1965)] in 90 ml. of dry pyridine 24.6 g. of methanesulphonic acid chloride are added dropwise, with stirring, under cooling with ice-water. The reaction mixture is allowed to stand at room temperature overnight, and the reaction mixture containing crystals is poured onto a mixture of 50 ml. of concentrated hydrochloric acid and 150 g. of ice. The oily phase is separated and the aqueous phase is extracted with two 100-ml. portions of ether. The ethereal solution is combined with the oil, it is shaken with two 100-ml. portions of a 1:1 mixture of hydrochloric acid and water, then washed to neutral with water and dried over sodium sulphate. Ether is distilled off and 2-methyl-6-allyl-phenol mesylester is obtained as a yellow oil. $n_D^{25} = 1.5252$.

EXAMPLE 14

To a solution of 4.28 g. of 3-(1-methyl)-allyl-4-hydroxy-benzophenone in 20 ml. of dry pyridine 2.2 g. of methane-sulphonic acid chloride are added, and the reaction mixture is heated on a water bath for five hours. The reaction mixture is cooled and is poured on the mixture of 10 ml. of concentrated hydrochloric acid and 100 g. of ice. The oily phase is shaken with three 50-ml. portions of ether. The combined ethereal extracts are shaken with three 20-ml. portions of 2N hydrochloric acid, washed to neutral with water, shaken with two 20-ml. portions of a 2N sodium hydroxide solution, washed with water again and finally dried over sodium sulphate. Evaporation of the product yields 3-(1-methyl)-allyl-4-mesyloxy-benzophenone as a yellow oil. $n_D^{22} = 1.5732$.

EXAMPLE 15

To a solution of 14.8 g. of 2-allyl-4-methyl-phenol [J. Am. Chem. Soc. 80, 3271 (1958)] in 50 ml. of dry pyridine 14 g. of methane-sulphonic acid chloride are added dropwise, with stirring, under cooling with ice-water. Furtheron the procedure described in Example 13 is followed. Distilling off the ether 2-allyl-4-methyl-phenolmesylester obtained as a yellow oil.

EXAMPLE 16

To a solution of 16.2 g. of 2-(1-methyl)-allyl-4-methyl-phenol [Helv. 45, 1943 (1962)] in 60 ml. of dry pyridine 18.43 g. of methanesulphonic acid chloride are added dropwise, with stirring, under cooling with ice-water. Furtheron following the procedure described in Example 13 and distilling off the ether 2-(1-methyl)-allyl-4-methyl-phenol mesylester is obtained as a yellow oil. $n_D^{28} = 1.5053$.

EXAMPLE 17

To a solution of 32.44 g. of 2-methyl-6-(1-methyl)-allyl-phenol in 120 ml. of dry pyridine 33.2 g. of methanesulphonic acid chloride are added dropwise, with stirring, under cooling with ice-water. Furtheron following the procedure described in Example 13 and distilling off ether 2-methyl-6-(1-methyl)-allyl-phenol mesylester is obtained, which is distilled in vacuo. Boiling point: 187° C. to 190° C./15 mmHg.; $n_D^{21} = 1.5283$.

EXAMPLE 18

7.17 g. of 2-(1-methyl-allyl)-4-phenoxy-phenol are dissolved in 30 ml. of pyridine and 3.41 g. of mesyl chloride are added dropwise, with cooling. The reaction mixture is allowed to stand in a refrigerator overnight, and is then poured onto a mixture of ice and 12 ml. of concentrated hydrochloric acid. The oily phase is shaken with three 20-ml. portions of benzene. From the combined benzene fractions unmesylated phenyl derivative is eliminated with two 20-ml. portions of Claisen-alkali, and the organic phase is washed to alkaline-free. The benzene solution is dried over sodium sulphate and is evaporated. Thus 2-(1-methyl-allyl)-4-phenoxy-phenyl-mesyl ester is obtained. $n_D^{22} = 1.5565$.

EXAMPLE 19

2 g. of 2-allyl-4-phenoxy-phenol are dissolved in 10 ml of pyridine and to the cooled solution 1 g. of mesyl chloride is added dropwise. The reaction mixture is allowed to stand overnight and is then poured onto a mixture of ice and 5 ml. of concentrated hydrochloric acid. The separated oil is eliminated by extraction with three 20-ml. portions of ether. The combined ethereal solutions are shaken with two 10-ml. portions of 1N sodium hydroxide, whereupon it is washed to neutral with water. The ethereal solution is dried over sodium sulphate. Evaporation of the product affords 2-allyl-4-phenoxy-phenyl mesylester.

EXAMPLE 20

To a solution of 7.7 g. of 3-allyl-4-hydroxy-benzophenone [J. Am. Chem. Soc. 80, 3271 (1958)] in 43 ml. of dry pyridine 4.46 g. of methanesulphonic acid chloride are added dropwise, with stirring, under cooling with ice-water. Furtheron the procedure described in Example 13 is followed. After distilling off ether 3-allyl-4-mesyloxy-benzophenone is obtained as a yellowish brown oil.

EXAMPLE 21

To a solution of 19.8 g. of potassium permanganate in 1500 ml. of acetone a solution of 5.3 g. of 2-allyl-phenol mesylester in 10 ml. of acetone is added dropwise, with stirring, under cooling. The reaction mixture is allowed to stand overnight, and thereafter is acidified with a 5N sulphuric acid solution and filtered. The filtrate is evaporated in vacuo. The crystalline residue is admixed with a sodium hydrogencarbonate solution, filtered and the filtrate is acidified with a 5N hydrochloric acid solution. The precipitated crystals are filtered off with suction to give 2-mesyloxy-phenyl-acetic acid, melting at 110° C. After recrystallization from a 50% ethanol solution the melting point amounts to 125° C. to 126° C.

EXAMPLE 22

To a suspension of 31.6 g. of potassium permanganate in 300 ml. of water a solution of 12.7 g. of 2-allyl-phenol mesylester, 60 ml. of acetic acid and 1.35 g. of tetrabutyl ammoniumchloride in 300 ml. of methylene chloride is added with stirring, under cooling with ice-water. The reaction mixture is stirred for 30 minutes with stirring, then 34 g. of sodium hydrogensulphite and 60 ml. of a 1:1 mixture of hydrochloride acid and water are added. The methylene chloride phase is separated and the aqueous phase is shaken with two 100-ml. portions of methylene chloride. The methylene chloride solution is dried over sodium sulphate. The crystalline substance obtained after distilling off methylene chloride is dissolved in 70 ml. of sodium hydrogencarbonate and the solution obtained is shaken with methylene chloride. The aqueous solution is acidified with a 2N aqueous hydrochloric acid solution. The precipitated crystals are filtered with suction and dried. Thus 2-mesyloxy-phenylacetic acid is obtained, melting at 123° C. to 124° C.

EXAMPLE 23

To a suspension of 15.8 g. of potassium permanganate in 150 ml. of water a solution of 6 g. of 2-(1-methyl)-allyl-phenol-mesylester, 30 ml. of acetic acid and 0.7 g. of tetrabutyl ammoniumchloride in 150 ml. of benzene is added with stirring, under cooling. Furtheron following the procedure described in Example 22 and filtering off the product obtained with suction 2-mesyloxy-hydratropic acid is prepared, melting at 94° C. to 96° C.

EXAMPLE 24

Following the procedure described in Example 22 but starting from 7.9 g. of 2-allyl-naphthol mesylester crystalline 1-mesyloxy-2-naphthyl-acetic acid is obtained, melting at 180° C. to 181° C.

EXAMPLE 25

Following the procedure described in Example 22 but replacing 2-allyl-phenol mesylester by 8.54 g. of 2-tosyloxy-phenylacetic acid 2-tosyloxy-phenylacetic acid is obtained, melting at 119° C. to 120° C.

EXAMPLE 26

To a suspension of 15.8 g. of potassium carbonate in 150 ml. of water 6.8 g. of 2-allyl-4-methyl mesylester are added under ice-cooling, with stirring. Furtheron following the procedure described in Example 22 2-mesyloxy-5-methylphenylacetic acid is obtained as a white crystalline substance. Recrystallization from a 50% aqueous ethanol solution affords a product melting at 101° C. to 102° C.

EXAMPLE 27

Following the procedure described in Example 22 but starting from 7.2 g. of 2-(1-methyl)-allyl-4-methyl-phenol mesylester 2-mesyloxy-5-methyl-hydratropic acid is obtained in the form of white crystals, melting at 122° C. to 123° C.

EXAMPLE 28

To a suspension of 8.4 g. of potassium permangaate in 84 ml. of water a solution of 3.3 g. of 3-(1-methyl)-allyl-4-mesyloxy-benzophenone, 0.34 g. of tetrabutyl ammonium chloride and 31 ml. of acetic acid in 84 ml. of benzene is added with stirring. Then following the procedure described in Example 22 a viscous substance is obtained, which is shaken with three 20-ml. portions of ether. Upon addition of cyclohexyl amine the cyclohexyl amine salt of 2-mesyloxy-5-benzoyl-hydratropic acid is obtained as a white crystalline substance, melting at 151° C.

EXAMPLE 29

To a suspension of 57.12 g. of potassium permanganate in 542 ml. of water a solution of 24.58 g. of 2-methyl-6-(1-methyl)-allyl-phenol mesylester, 2.42 g. of tetrabutyl ammoniumchloride and 216 ml. of acetic acid in 542 ml. of benzene is added with stirring, under cooling with ice-water. Then following the procedure described in Example 22 2-mesyloxy-3-methyl-hydratropic acid precipitates as a white crystalline substance. The crystals are filtered off with suction. Melting point: 138° C. to 142° C.

EXAMPLE 30

To a suspension of 25.6 g. of potassium permanganate in 250 ml. of water a solution of 9.2 g. of 3-allyl-4-mesyloxy-benzophenone, 1 g. of tetrabutyl ammoniumchloride and 90 ml. of acetic acid in 250 ml. of benzene is added at room temperature with stirring. Furtheron following the procedure described in Example 22 2-mesyloxy-5-benzoylphenylacetic acid is obtained as a white crystalline product. After filtering off with suction and recrystallization from abs. ethanol the product melts at 154° C. to 155° C.

EXAMPLE 31

To a suspension of 33.2 g. of potassium permanganate in 315 ml. of water a solution of 14.2 g. of 2-methyl-6-allyl-phenol mesylester, 126 ml. of acetic acid and 1.4 g. of tetrabutyl ammoniumchloride in 315 ml. of benzene is added with stirring, under cooling with ice-water. Then following the procedure described in Example 22 2-mesyloxy-3-methyl-phenylacetic acid is obtained as a white crystalline product, melting at 121° C. to 124° C.

EXAMPLE 32

6.85 g. of 2-(1-methyl-allyl)-4-phenoxy phenylmesylester are dissolved in 180 ml. of benzene containing 0.73 g. of tetrabutyl ammoniumchloride and 67 ml. of glacial acetic acid. The solution obtained is added to a solution of 19 g. of potassium permanganate in 180 ml. of water with stirring. Then following the procedure described in Example 22 a slowly solidifying oily product is obtained. Melting point of the crystalline product obtained after standing amounts to 113° C. to 118° C. After recrystallization from 30 ml. of diisopropyl ether the melting point of 2-mesyloxy-5-phenoxyhydratropic acid is 123° C. to 125° C.

EXAMPLE 33

1.53 g. of 2-allyl-4-phenoxy phenylmesylester are dissolved in 47 ml. of benzene containing 0.2 g. of tetrabutyl ammoniumchloride and 17 ml. of glacial acetic acid. The solution obtained in poured into a solution of 5 g. of potassium permanganate in 47 ml. of water. Then following the procedure described in Example 22 an oily product is obtained, which is dissolved in a 1N solution of sodium hydrogencarbonate. The solution obtained is shaken with two 10-ml. portions of benzene, whereupon the alkaline phase is acidified with a concentrated hydrochloric acid solution and shaken with three 10-ml. portions of ether. The combined ethereal extracts are dried and evaporated to give 2-mesyloxy-5-phenoxy phenylacetic acid, melting at 121° C.

EXAMPLE 34

To a solution of 33 g. of 2-methane-sulphonyloxy-3-phenoxy-hyratropic acid in 200 ml. of methanol 28 ml. of triethyl amine and 2 g. of a 5% palladium on charcoal catalyst are added at 25° C. The mixture is then hydrogenated under atmospheric pressure until a calculated amount of hydrogen is used up. The catalyst is filtered off and the solution is evaporated. The evaporation residue is taken up in water, acidified with a 20% aqueous hydrochloric acid solution and the separated oil is extracted with chloroform. The chloroform solution is evaporated after drying over sodium sulphate, and the residue is distilled off. 23 g. (95%) of 3-phenoxy-hydratropic acid are obtained, boiling at 190° C. to 192° C. (0.4 mmHg.). $n_D^{25}=1.5751$ Melting point of the corresponding cyclohexylamine salt amounts to 153° C. to 154° C.

EXAMPLE 35

Following the procedure described in Example 34 but starting from 32.5 g. of 2-(1-methane-sulphonyloxy-6-methoxy-2-naphthyl)propionic acid, 34 g. of 2-methanesulfphonyloxy-4-phenyl-5-fluoro-hydratropic acid, 35 g. of 2-methanesulfphonyloxy-5-benzoyl-hydratropic acid and 24.5 g. of 1-methane-sulphonyloxy-2-naphthyl-acetic acid, respectively the following end products are obtained:

| End product | melting point (°C.) |
| --- | --- |
| 22 g. of 2-(6-methoxy-2-naphthyl)-propionic acid | 153 to 155 |
| 23.3 g. of 3-fluoro-4-phenyl-hydratropic acid | 110 to 111 |
| 24.4 g. of 3-benzoyl-hydratropic acid | 90 to 92 and |
| 16 g. of 2-naphthyl-acetic acid | 141 to 142, resp |

EXAMPLE 36

To a solution of 77.5 g. of 2-methane-sulphonyloxy-4-methyl-hydratropic acid in 600 ml. of methanol 84 ml. of triethyl amine and 6 g. of a 5% palladium on charcoal catalyst are obtained, and the mixture is hydrogenated at 25° C. until a calculated amount of hydrogen is used up. Catalyst is filtered off and the filtrate is evaporated. The residue is taken up in water and the solution is acidified with a 20% aqueous hydrochloric acid solution. The separated 4-methyl-hydratropic acid is extracted with chloroform and the chloroform extract is dried over sodium sulphate. Evaporation of the solution affords 4-methylhydratropic acid.

EXAMPLE 37

To a solution of 24.5 g. of 2-methane-sulphonyloxyhydratropic acid in 200 ml. of methanol 28 ml. of triethylamine and 2 g. of a 5% palladium-on-charcoal catalyst are added. The mixture is hydrogenated at 25° C., under atmospheric pressure until a calculated amount of hydrogen is used up. The catalyst is filtered off and the filtrate is evaporated. The residue is taken up in water and acidified with a 20% aqueous hydrochloric acid solution. The separated hydratropic acid is extracted with chloroform. The chloroform solution is dried over sodium sulphate, evaporated and the residue is distilled off. 13.5 g. (90%) of hydratropic acid are obtained, boiling at 145° C. (13 mmHg.); $n_D^{25} = 1.5219$.

EXAMPLE 38

To a solution of 4.1 g. of 2-toluene-sulphonyloxy-3-phenoxy-hydratropic acid in 150 ml. of alcohol 24 g. of a W-6 nickel catalyst are added, and the mixture is hydrogenated at 25° C., under atmospheric pressure until a calculated amount of hydrogen is used up. The catalyst is filtered off, the filtrate is evaporated and the residue is taken up in water and acidified with a 10% aqueous hydrochloric acid solution. The separated oil is extracted with chloroform, the chloroform solution is dried over sodium sulphate and evaporated. 2.1 g. (89%) of 3-phenoxy-hydratropic acid are obtained. Melting point of the corresponding cyclohexylamine salt amounts to 151° C. to 153° C.

EXAMPLE 39

To a solution ofm 3.3 g. of 2-toluene-sulphonyloxy-4-methyl-hydratropic acid in 150 ml. of alcohol 15 g. of Raney nickel are added as a catalyst and the reaction mixture is boiled for three hours with stirring. Upon cooling the catalyst is filtered off and the filtrate is evaporated. The residue is triturated with 50 ml. of water and the separated product is extracted with chloroform. Evaporation of the chloroform extract affords 1.5 g. (91%) of 4-methyl-hydratropic acid.

EXAMPLE 40

To a solution of 3.4 g. of 2-amino-sulphonyloxy-3-phenoxy-hydratropic acid in 20 ml. of methanol 2.8 ml. of triethylamine and 0.2 g. of a 5% palladium-on-charcoal catalyst are added. The mixture is hydrogenated at 25° C., under atmospheric pressure until a calculated amount of hydrogen is used up. The catalyst is filtered off and the filtrate is evaporated. The evaporation residue is taken up in water, acidified with a 20% aqueous hydrochloric acid solution and the separated oil is extracted with chloroform. The chloroform extract is dried over sodium sulphate and is evaporated to give 2.2 g. (91%) of 3-phenoxy-hydratropic acid. Melting point of the corresponding cyclohexylamine salt amounts to 151° C. to 153° C.

EXAMPLE 41

Following the procedure described in Example 40 but starting from
4.5 g. of 2-(N-benzoylamino-sulphonyloxy)-5-benzoyl-hydratropic acid;
3.8 g. of 2-[1-(N-methoxy-carbonylamido-sulphonyloxy)-6-methoxy-2-naphthyl]-propionic acid and
2.44 g. of 2-mesyloxy-3-methyl-phenylacetic acid, respectively the following end products are obtained:

| End product | Melting point (°C.) |
|---|---|
| 2.35 g. of 2-benzoyl-hydratropic acid | 90 to 92 |
| 2.2 g. of 2-(6-methoxy-2-naphthyl)-propionic acid | 153 to 155 |
| 3-methyl-phenylacetic acid | 67 to 69, resp. |

EXAMPLE 42

To a solution of 4.2 g. of 2-hydroxy-3-phenoxy-hydratropic acid sulphate dipotassium salt in 50 ml. of water 2 g. of potassium hydroxide and 2 g. of a Raney nickel catalyst prepared freshly according to Urashibara, and the reaction mixture is stirred at 60° C. for 10 to 15 minutes. The catalyst is filtered off and the filtrate is acidified with a 20% aqueous hydrochloric acid solution. The separated solution is extracted with chloroform and the chloroform solution is dried over sodium sulphate and evaporated. 2.35 g. (97%) of 3-phenoxy-hydratropic acid are obtained. Melting point of the corresponding cyclohexylamine salt: 151° C. to 153° C.

EXAMPLE 43

To a solution of 3.4 g. of 2-hydroxy-4-methyl-hydratropic acid sulphate dipotassium salt in 50 ml. of water Raney nickel is added as a catalyst, and the mixture is hydrogenated until the calculated amount of hydrogen is used up. The catalyst is filtered off and the filtrate is acidified with a 20% aqueous hydrochloric acid solution. The separated oil is extracted with chloroform. Evaporation of the chloroform extract affords 1.5 g. (91.5%) of 4-methyl-hydratropic acid.

EXAMPLE 44

3.8 g of 2-(N,N'-dicyclohexyl-isocarbamido)-4-methyl-hydratropic acid are dissolved in isopropanol and to the solution obtained 0.2 g. of a 5% palladium-on-charcoal catalyst are added. The mixture is then hydrogenated at 25° C., under atmospheric pressure until the calculated amount of hydrogen is used up. Catalyst is filtered off and the filtrate is evaporated. The residue is treated with a 5% sodium carbonate solution and is filtered. The filtrate is acidified with a 20% aqueous hydrochloric acid solution and the separated oil is extracted with chloroform. The chloroform extract is dried over sodium sulphate, dried and evaporated. 1.4 g. (85%) of 4-methyl-hydratropic acid are obtained.

EXAMPLE 45

3 g. of 2-hydroxy-4-methyl-hydratropic acid phenylurethane are dissolved in acetic acid. To the solution 0.4 g. of a 5% palladium-on-charcoal catalystand the mixture is hydrogenated at 25° C. until the calculated amount of hydrogen is used up. The catalyst is filtered off and the filtrate is evaporated. The residue is admixed with a 10% aqueous hydrochloric acid solution and the separated oil is extracted with chloroform. The chloroform solution is dried over sodium sulphate and evaporated. 1.1 g. (67%) of 4-methyl-hydratropic acid are obtained.

EXAMPLE 46

3.2 g. of [5-methyl-2-(1-carboxy-1-ethyl)-phenyl](1-phenyl)-5-tetrazolyl ether are dissolved in 100 ml. of benzene and to the solution obtained 0.8 g. of a 5% palladium-on-charcoal catalyst are added. The mixture is hydrogenated at 35° to 40° C., under a pressure of 2.8 atm., until the calculated amount of hydrogen is used up. The catalyst is filtered off and washed with hot ethanol. The filtrate is evaporated and the residue is treated with a 5% solution sodium carbonate solution. After filtration the filtrate is acidified with a 20% aqueous hydrochloric acid solution and the separated oil is extracted with chloroform. The chloroform solution is dried over sodium sulphate and evaporated. 1.4 g. (85%) of 4-methylhydratropic acid are obtained.

EXAMPLE 47

To a solution of 1.29 g. of 2-mesyloxy-5-methyl-hydratropic acid in 25 ml. of methanol 1.4 ml. of triethylamine and 0.2 g. of a 5% palladium-on-charcoal catalyst are added. The mixture is hydrogenated at 25° C., under atmospheric pressure until the calculated amount of hydrogen is used up. The catalyst is filtered off and the solution is evaporated. The evaporation residue is taken up in water, acidified with a 20% aqueous hydrochloric acid solution and shaken with ether. Ether is distilled off to give 3-methyl-hydratropic acid as an oily residue. The corresponding cyclohexylamine salt melts at 168° C. to 169° C.

EXAMPLE 48

1.22 g. of 2-mesyloxy-5-methyl-phenylacetic acid are dissolved in 20 ml. of methanol and to the solution obtained 1.4 ml. of triethyl amine and 0.2 g. of a 5% palladium-on-charcoal catalyst are added. Then following the procedure described in Example 47 a white, crystalline product is obtained, melting at 64° C. to 65° C. The product obtained is 5-methyl-phenylacetic acid.

What we claim is:

1. A process for the preparation of a compound of the formula (I)

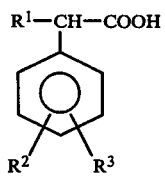

wherein
$R^1$ is hydrogen, methyl or ethyl;
$R^2$ is hydrogen, fluoro, or alkyl having 1 to 4 carbon atoms;
$R^3$ is hydrogen, phenyl, alkoxy having 1 to 6 carbon atoms, phenoxy, thenoyl or benzoyl; or
$R^2$ and $R^3$ together with the phenyl group to which they are attached form a naphthyl group which is unsubstituted or substituted by $C_1$ to $C_4$ alkyl or $C_1$ to $C_4$ alkoxy; which comprises the steps of:
(a) reacting a compound of the formula (V)

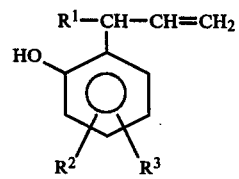

with a complex of the formula (X)

wherein
$R^8$ is $C_1$ to $C_4$ alkyl; and
$R^9$ is $C_1$ to $C_4$ alkyl or phenyl, in an organic solvent at a temperature of 10° to 40° C., and subsequently treating the reaction mixture with an aqueous solution of an inorganic base, to yield a compound of the formula XVIa

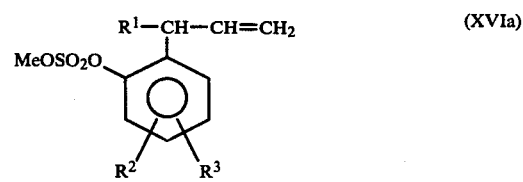

wherein Me is selected from the group consisting of sodium ion and potassium ion;
(b) oxidizing the compound of the formula (XVIa) in a solvent to yield a component of the formula XVIb

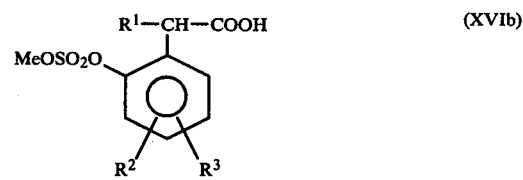

and
(c) catalytically hydrogenating the compound of the formula XVIb to yield the desired product.

2. The process defined in claim 1, wherein in step (a), the complex of the formula X is the sulfur trioxide complex of N,N-dimethyl-aniline, N,N-diethyl-aniline, or trimethyl-amine.

3. The process defined in claim 1, wherein in step (a), the organic solvent is carbon disulfide or benzene.

4. The process defined in claim 1, wherein in step (a), the inorganic base is sodium hydroxide or potassium hydroxide added in excess amount.

5. The process defined in claim 1, wherein in step (b), the oxidation is carried out with potassium permanganate or an alkali metal periodate.

6. The process defined in claim 1, wherein in step (b), the solvent is water or an organic solvent.

7. The process defined in claim 1, wherein in step (b), the oxidation is carried out in the presence of a phase-transforming catalyst and acetic acid.

* * * * *